United States Patent [19]

Stober et al.

[11] 4,287,135

[45] Sep. 1, 1981

[54] STABILIZED DIPEROXYALKANEDIOIC ACIDS AND AROMATIC PEROXYCARBOXYLIC ACIDS

[76] Inventors: Reinhard Stober, Ludwig Uhlandstr. 7, 6451 Gross-Krotzenburg; Rolf Wirthwein, Fuerstenbergstr. 4, 6450 Hanau 9; Christian Hase, Millrather Weg 29, 4006 Erkrath 9, all of Fed. Rep. of Germany

[21] Appl. No.: 83,654

[22] Filed: Oct. 11, 1979

Related U.S. Application Data

[63] Continuation-in-part of Ser. No. 954,590, Oct. 25, 1978, abandoned.

[51] Int. Cl.$^3$ ............................................. C07C 179/10
[52] U.S. Cl. ................................ 260/502 R; 252/186; 568/559
[58] Field of Search .................... 568/559, 563, 561; 252/186; 260/502 R

[56] References Cited

U.S. PATENT DOCUMENTS

| | | | |
|---|---|---|---|
| 2,207,737 | 7/1940 | Hooft et al. ........................... | 252/186 |
| 2,222,830 | 11/1940 | Moss ..................................... | 252/186 |
| 2,639,298 | 5/1953 | Head ..................................... | 568/755 |
| 2,813,896 | 11/1957 | Krimm .............................. | 260/502 R |
| 3,770,816 | 11/1973 | Nielsen .............................. | 260/502 R |
| 4,094,808 | 6/1978 | Stewart et al. ........................ | 252/186 |
| 4,126,850 | 11/1978 | Johnston ............................... | 252/186 |
| 4,128,490 | 12/1978 | Finley et al. .......................... | 252/186 |
| 4,134,850 | 1/1979 | McCrudden .......................... | 252/186 |
| 4,170,453 | 10/1979 | Kitko ............................... | 260/502 R |

FOREIGN PATENT DOCUMENTS

| | | | |
|---|---|---|---|
| 560389 | 9/1957 | Belgium .................................. | 260/502 |
| 635620 | 1/1962 | Canada .................................... | 252/186 |
| 1468847 | 8/1970 | Fed. Rep. of Germany ........... | 260/502 |
| 1668569 | 3/1972 | Fed. Rep. of Germany ........... | 260/502 |
| 1668370 | 7/1972 | Fed. Rep. of Germany . | |
| 2422691 | 5/1974 | Fed. Rep. of Germany .......... | 252/186 |
| 2422735 | 12/1974 | Fed. Rep. of Germany .......... | 252/186 |
| 2129034 | 10/1972 | France . | |

OTHER PUBLICATIONS

Swern "Organic Peroxides" vol. 1, II and III (1970–1972) pp. 388–392 Wiley-Interscience, N.Y.
Swern "J.A.C.S." vol. 77, pp. 5537–5555 4/1 (1955).
Parker, "J.A.C.S." vol. 79, pp. 1929–1931 (1955).

*Primary Examiner*—Werren B. Lone
*Attorney, Agent, or Firm*—Cushman, Darby & Cushman

[57] ABSTRACT

Diperoxyalkanedioic acids and aromatic peroxycarboxylic acids are prepared by reacting a dialkanoic acid or an aromatic carboxylic acid with hydrogen peroxide in sulfuric acid and then producing a desensitizing agent for the peracid in situ by adding alkali metal hydroxide, alkali metal aluminate or an alkaline earth metal hydroxide so that the filtrate is free of sulfuric acid. The resulting salt coats the peracid and the product is desensitized and stable in storage.

31 Claims, No Drawings

STABILIZED DIPEROXYALKANEDIOIC ACIDS AND AROMATIC PEROXYCARBOXYLIC ACIDS

CROSS-REFERENCE TO RELATED APPLICATION

This application is a continuation-in-part of application Ser. No. 954,590 filed Oct. 25, 1978, now abandoned, the entire disclosure of which is hereby incorporated by reference.

BACKGROUND OF THE INVENTION

The present invention is directed to the production of desensitized and storage stable, aliphatic diperoxyalkanedioic acids, and aromatic peroxycarboxylic acids.

Solid, water insoluble, peroxycarboxylic acids showed thermal and mechanical sensitivity when in the pure or highly concentrated condition. Various methods are described in the literature for the safe handling of these compounds (D. Swern Organic Peroxides Vols. I, II and III, 1970-1972: R. Criegee in Houben—Weyl Vol. 8). Methods of preparing diperoxyalkanedioic acids are disclosed in Swern, Organic Peroxides Vol. I, pages 388-392 and the references cited therein as well as McCune, Canadian Pat. No. 635,620. Methods of preparing aromatic peroxycarboxylic acids are disclosed in German application No. P 29 29 839.3, July 23, 1979.

A desensitization can also be provided under certain conditions by the addition of alkali, alkaline earth, aluminium and ammonium salts of strong mineral acids as, e.g. sulfuric acid.

Thereby there have already been attempts to further lower the tendency to decomposition or spontaneous decomposition by using salts which were low in water of hydration in order that the thus stabilized peroxycarboxylic acids could take up moisture occuring in storage, see Belgian Pat. No. 560,389. Conversely it has also already been proposed to reduce the tendency to decomposition through such of the above mentioned salts which form hydrates and by mixing them in their hydrate form, see German Pat. No. 1,468,847.

According to the process of German AS No. 1,668,569 and German Pat. No. 1,668,570 it was proposed to feed peroxycarboxylic acids dispersed in water into a fluidized bed of a salt hydrate. Thereby the particles of the percarboxylic acids should be coated with a jacket of the hydrate. However, there are placed quite specific requirements on the hydrate in reference to the temperatures at which the water of crystallization is first permitted to be given up or there can only be employed very specific hydrates.

The jackets built thereby, however, were not without flaws, entirely apart from the fact that the process was very expensive and the mixture were inclined to cake together.

Therefore in recent times there has again been a return to the simple mixture of the dry acid or water wet acid with the dry salts.

However, a sure desensitization can only occur if there is present a homogeneous and dilute mixture.

In a process such as that described for example in McCune Canadian Pat. No. 635,620 and Gougeon German OS No. 2,422,691 and Gougeon German OS No. 2,422,735, the desensitizing agent is mixed in subsequently. As a result of this, there is the danger of a partial inhomogeneity. A further disadvantage is that the dry mixing of a high percentage of peroxy acid with the desensitizing agent under some circumstances leads to a higher mechanical sensitivity which is produced by the shearing effects on the edges of the crystals.

SUMMARY OF THE INVENTION

The disadvantages of the prior art procedures are avoided and a desensitized product which is stable in storage is obtained if the desensitizing agent is produced in situ in the reaction mixture resulting from the reaction of an alkanedioic acid having 5 to 16 carbon atoms, preferably 5 to 12 carbon atoms, which can be straight chained, branched or substituted with groups of alkoxy, halogen, nitro and sulfanic acid with hydrogen peroxide in sulfuric acid solution. Such desensitizing agents including for example alkali metal, alkali metal aluminum sulfates and alkaline earth metal sulfates, preferably $Na_2SO_4$, $MgSO_4$ and sodium aluminium sulfate or mixtures thereof, although there can also be employed potassium sulfate, calcium sulfate and lithium sulfate.

It has further been found that in place of the alkanedioic acid there can be employed aromatic carboxylic acids to form desensitized aromatic percarboxylic acids. The aromatic carboxylic acids have the formula

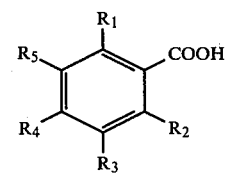

wherein $R_1$, $R_2$, $R_3$, $R_4$ and $R_5$ are hydrogen, COOH, 1-4 carbon atom alkyl, 1-4 carbon atom alkoxy and/or halogen e.g. chlorine, fluorine or bromine.

The desensitizing agent is formed in situ by addition sodium hydroxide, magnesium hydroxide, calcium hydroxide, lithium hydroxide, potassium hydroxide or sodium aluminate, e.g. as a 5 to 50% aqueous solution or suspension to the reaction mixture of the alkanedioic acid or aromatic carboxylic acid, hydrogen peroxide and sulfuric acid at a temperature which is usually 0°-30° C., preferably 15°-20° C., more preferably 18°-20° C. until a pH of 2-6, preferably 5-5.5 is obtained. There is obtained a homogeneous mixture of diperoxyalkanedioic acid or aromatic peroxy carboxylic acid particles coated with (i.e. encased in) the inorganic salt formed. Mixtures of desensitizing agents can be formed in situ, e.g. employing a mixture of sodium and magnesium hydroxides.

The reaction between the alkanedioic acid and the hydrogen peroxide in sulfuric acid can take place in conventional manner. However, the reaction between the aromatic acid and hydrogen peroxide in sulfuric acid is carried out according to process, disclosed in German application P No. 29 29 839.3, loc. cit. The hydrogen peroxide is normally used in excess. Thus there can be used for example from 2 to 20 moles of hydrogen peroxide per mole of alkanedioic acid or aromatic carboxylic acid. The concentration of the alkanedioic acid or aromatic carboxylic acid is not critical. For example, there can be used from 10 to 300 parts by weight of alkanedioic acid or aromatic carboxylic acid per 100 parts by weight of sulfuric acid, calculated as 100% $H_2SO_4$ by weight.

The concentration of the hydrogen peroxide is not critical and it can be employed in conventional concentration, e.g. 30 to 99% for alkanedioic acids and 50-99% for aromatic acids.

Also, the exact concentration of the sulfuric acid is not critical although it is normally concentrated. (It will be noted that the aqueous hydrogen peroxide has a diluting effect). It can be employed in conventional concentration, e.g. 20 to 95% by weight, preferred is a concentration of 90-95% by weight.

As alkanedioic acids there can be used for example glutaric acid, adipic acid, pimelic acid, suberic acid, azelaic acid, 1,10-decanedicarboxylic acid, 1,12-dodecandicarboxylic acid and 1,14-tetradecanedicarboxylic acid.

Examples of aromatic carboxylic acids are benzoic acid, o-phthalic acid, isophthalic acid, terephthalic acid, mellitic acid, hemimellitic acid, trimellitic acid, trimesic acid, prehnitic acid, pyromellitic acid, benzenepentacarboxylic acid, o-toluic acid, m-toluic acid, p-toluic acid, o-chlorobenzoic acid, p-chlorobenzoic acid, m-chlorobenzoic acid, p-bromobenzoic acid, o-fluorobenzoic acid, o-fluorobenzoic acid, 2,4-dichlorobenzoic acid, 2-methyl-4-chlorobenzoic acid, p-ethyl benzoic acid, p-butyl benzoic acid, p-methoxy benzoic acid, p-butoxy benzoic acid, o-ethoxy benzoic acid, 1-methyl-2,4-dicarboxybenzene, 2,4-dimethyl benzoic acid.

The preferred aromatic carboxylic acids are benzoic acid, the phthalic acids, the benzene tri and higher polycarboxylic acids, as e.g. mellitic acid. The most preferred aromatic carboxylic acid is isophthalic acid.

The effects of the process of the present invention, e.g. the dilution and the coating, besides creating good stability in storage also greatly reduce the thermal and mechanical sensitivity. An advantage of the process of the invention is that no sulfuric acid is obtained in the filtrate after the separation. For that reason no pollution problems occur.

An advantage of the process of the invention is that not only is there formed an effective homogeneous mixture of the peroxycarboxylic acid and the desensitizing agent but the particles of peroxycarboxylic acid are completely encased, through which even with damage to a particle jacket and beginning decomposition of the peroxyacid particle there is not possible a continuation of the decomposition.

Furthermore through the in situ formation of the desensitizing agent the mineral acid present is immediately used to desensitization of the peroxycarboxylic acid formed. Difficulties which occurred up to now with the diluted aqueous mineral acid resulting when adding the desensitizing agent after the production of the peroxy carboxylic acid and its separation from the reaction mixtures, which must either be worked up or rejected which cause environmental problems are eliminated by the process of the invention.

The desensitizing method of the invention described above was tested with diperoxyadipic acid, diperoxysuberic, diperoxyazelaic and diperoxy isophthalic acid wherein outstanding results were obtained. Examples for the storage stability of different concentrations of diperoxyazelaic acid are shown in the following table:

TABLE 1

| Weight % peroxyacid | Weight % peroxy acid | % Decomposition |
|---|---|---|
| 0 days | 14 days | In 14 days |
| 26.5 | 26.2 | 1.3 |
| 34.6 | 34.2 | 1.2 |
| 47.7 | 47.3 | 1.0 |

TABLE 1-continued

| Weight % peroxyacid | Weight % peroxy acid | % Decomposition |
|---|---|---|
| 85.4 | 84.4 | 1.2 |

The mechanical sensitivity was obtained by standard drop weight tests according to the known method of the "Bundesanstalt für Materialprüfung (BAM)" (Federal Institute for Testing Material of the Federal Republic of Germany). For this purpose some of the samples of desensitized diperoxyazelaic acid were air dried and some were dried in a vacuum at 40°-50° C. over a convention drying agent. In no case in the complete removal of the residual water was there noted an increase in the sensitivity of the sample.

The influence of the coating of the peroxyacid particles by the desensitizing agent is shown by a comparison of the maximum impact energy obtained in the standard drop weight test, which is a measure of the mechanical sensitivity of the samples prepared, using two samples of 85 weight % diperoxyazelaic acid, sample A was not desensitized and was made according to the method of Parker, J. Amer. Chem. Soc. Vol. 79, pages 1929-1931 (1957) and Swern, J. Amer. Chem. Soc. Vol. 77, pages 5537-5541 while sample B was synthesized by the process of the invention.

TABLE 2

|  | Maximum Impact Energy (mkg) |
|---|---|
| 85% A | 0.7 |
| 85% B | 2.0 |
| 54% C | 0.7 |

As a comparison, there is given the value for a 45% diperoxyazelaic acid (C). This composition C was obtained by dry mixing of 92 weight % diperoxyazelaic acid with dry sodium sulfate. The treatment with the desensitizing agent can take place batchwise or continuously.

Unless otherwise indicated, all parts and percentages are by weight.

The process can comprise, consist essentially of, or consist of the steps set forth employing the materials set forth.

DESCRIPTION OF THE PREFERRED EMBODIMENTS

EXAMPLE 1

A cooled mixture of 743 grams of hydrogen peroxide (50%) and 561 grams of concentrated (95%) sulfuric acid were treated within 15 minutes with 414 grams of solid, pulverized azelaic acid and stirred for 20 hours at room temperature. The thus obtained sulfuric acid reaction mixture was subsequently treated with the calculated amount of 30% aqueous sodium hydroxide solution to give an encased, precipitated diperoxyazelaic acid, which was filtered. After drying the filter residue there were obtained 508 grams of diperoxyazelaic acid desensitized with $Na_2SO_4$. The analysis showed a peroxyacid content of 85 weight % and a residual water content of 3 weight %.

EXAMPLE 2

The reaction mixture produced in accordance with Example 1 from 565 grams of pulverized azelaic acid, 1020 grams of 50% aqueous hydrogen peroxide and 817 grams of concentrated (95%) sulfuric acid was treated with 35% aqueous Mg (OH)₂ slurry until a pH of 5.0 was obtained. The temperature was held at 18°-20° C. Filtering and drying the product to constant weight gave 509 g with 34.6 weight % of diperoxyazelaic acid, desensitized with MgSO₄. Residual water content 1 weight %.

EXAMPLE 3

To a reaction mixture produced according to Example 1 from 226 grams of pulverized azelaic acid, 410 grams of 50% aqueous H₂O₂ and 326 grams of concentrated (95%) H₂SO₄ there were added 796 grams of 30% aqueous NaOH solution with stirring. The pH of the final mixture was 5.2. Filtering and drying in a vacuum to constant weight resulted in 671 g of a Na₂SO₄ desensitized diperoxyazelaic acid. The peroxyacid content was 26.5 weight %. Residual water content less than 1 weight %.

EXAMPLE 4

50 grams (0.34 moles) of adipic acid were dissolved in 40 ml concentrated sulfuric acid. This solution was added to a cooled mixture of 80 ml concentrated sulfuric acid and 93.1 grams (1.37 moles) of 50% aqueous hydrogen peroxide. The temperature of the reaction mixture increased to 45°. Stirring was continued for an additional 15 minutes.

After the addition of 50 ml water the reaction mixture was treated with an aqueous slurry of Mg(OH)₂ until a pH-value of 4 was obtained. The solids were separated by filtration and dried. The yield was 165 grams of diperoxyadipic acid, desensitized with MgSO₄ (content of peroxyacid: 20.0%).

EXAMPLE 5

As described in example 4 50 grams (0.22 moles) of 1.12-dodecanoic acid was mixed with 59 grams (0.87 moles) of 50% aqueous hydrogen peroxide in 120 ml concentrated sulfuric acid. After 15 minutes the reaction mixture was cooled and treated with an aqueous solution of sodium aluminate, produced by mixing 200 grams of Al(OH)₃, 305 grams of 50% aqueous NaOH and 600 ml of water. After obtaining a pH-value of 3.7 the solids were separated by filtration. Drying the filter cake 124 grams of diperoxydodecanoic acid, desensitized with sodium aluminum sulfate were obtained. The content of peroxyacid is 34.9%.

EXAMPLE 6

As described in example 4 50 grams (0.27 moles) of azelaic acid were treated with 72.3 grams (1.06 moles) of 50% aqueous hydrogen peroxide in 70 ml of concentrated sulfuric acid. After the addition of 170 grams of an aqueous solution of MgSO₄ the reaction mixture was cooled and treated with an aqueous solution of Mg(OH)₂ until a pH-value of 3 was obtained. The solids were separated by filtration and after drying there were obtained 99.5 grams of diperoxyazelaic acid, desensitized with MgSO₄. The content of peroxy-acid is 39.2%.

EXAMPLE 7

The sulfuric acid reaction mixture obtained from the reaction of 99.7 grams of isophthalic acid (0.6 mole) with 120 grams of 85 weight % hydrogen peroxide (3.0 moles) and 306 grams of 96 weight % sulfuric acid (3.0 moles) were treated at 5° C. and with continuous stirring with 30 weight % aqueous NaOH up to a pH of 4. After filtration and drying there were obtained 376 grams of product with a diperoxyisophthalic acid (DPIP) content of 21.1 weight % corresponding to a yield of 66.7% of theory.

EXAMPLE 8

To the sulfuric acid reaction mixture obtained from the reaction of 99.7 grams of isophthalic acid (0.6 mole) with 96 grams of 85 weight % hydrogen peroxide (2.4 moles) and 245 grams of 96 weight % sulfuric acid (2.4 moles) there were added 700 ml of saturated sulfuric acid solution, the mixture cooled to 5° C. and the mixture treated with 30 weight % NaOH until a pH of 4 was obtained. After filtration and drying there were obtained 333 grams of product having a content of DPIP of 22.9 weight %, corresponding to a yield of 59.2% of theory.

EXAMPLE 9

The sulfuric acid reaction mixture obtained according to Example 7 in a manner analogous to Example 7 was treated with 30 weight % of aqueous KOH until a pH of 5 and worked up as in Example 7. There were obtained 423 grams of product with a DPIP content of 18.0 weight %, corresponding to a yield of 64.0% theory.

EXAMPLE 10

In the manner described in Example 7 the sulfuric acid reaction mixture was treated with 30 weight % of aqueous LiOH suspension to a pH of 5 and worked up in a manner analogous to Example 7.

There were obtained 271.3 grams of product with a DPIP content of 33.9 weight %, corresponding to a yield of 77.4% of theory.

EXAMPLE 11

In the manner described in Example 7 the sulfuric acid reaction mixture was treated with 30 weight % of an aqueous Mg(OH)₂ suspension to a pH of 5 and worked up in a manner analogous to Example 7.

There were obtained 202.8 grams of product with a DPIP content of 20.9 weight %, corresponding to a yield of 71.3% of theory.

EXAMPLE 12

In the manner described in Example 7 the sulfuric acid reaction mixture was treated with 30 weight % of sodium aluminate suspension to a pH of 4 and worked up in a manner analogous to Example 7. There were obtained 476 grams of product with a DPIP content of 21.8 weight %, corresponding to a yield of 87.3% of theory.

EXAMPLE 13

In the manner described in example 7 the sulfuric acid reaction mixture was treated with 30 weight % of an aqueous Ca(OH)₂ suspension to a pH of 6 and worked up in a manner analogous to example 7. There were obtained 572 g of product with a DPIP content of 1.3 weight %.

EXAMPLE 14

In the manner described in example 7 the sulfuric acid reaction mixture was treated with 30 weight % of aqueous LiOH suspension to a pH of 2 and worked up in an manner analogous to example 7. There were obtained 356 g of product with a DPIP content of 85.1 weight %, corresponding to a yield of 75.4% of theory.

What is claimed is:

1. A process for the production of a peroxy acid which is storage stable and desensitized comprising adding to the mixture resulting from the reaction of an alkanedioic acid having at least five carbon atoms or an aromatic carboxylic acid having the formula

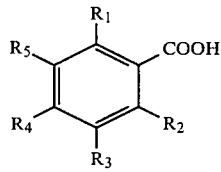

wherein $R_1$, $R_2$, $R_3$, $R_4$ and $R_5$ are hydrogen, COOH, 1-4 carbon atom alkyl, 1-4 carbon atom alkoxy or halogen with hydrogen peroxide in sulfuric acid a material which reacts with sulfuric acid to form a sulfate salt as a desensitizing agent, said material being an alkali metal hydroxide, an alkaline earth metal hydroxide or sodium aluminate and being added in an amount to raise the pH to 2-6.

2. A process according to claim 1 for the production of a diperoxyalkanedioic acid which is storage stable and desensitized comprising adding to the mixture resulting from the reaction of an alkanedioic acid having at least five carbon atoms with hydrogen peroxide in sulfuric acid a material which reacts with sulfuric acid to form a sulfate salt as a desensitizing agent.

3. The process of claim 2 wherein the added material is added in aqueous solution or suspension.

4. The process of claim 3 wherein the added material is an aqueous solution of sodium hydroxide, aqueous slurry of magnesium hydroxide or aqueous solution or slurry of sodium aluminate.

5. The process of claim 4 wherein the added material is employed in an amount to give a solid diperoxyacid having a peroxyacid content of 2.5 to 85.4%.

6. The process of claim 5 wherein the starting dialkanoic acid is azelaic acid.

7. The process of claim 4 wherein the starting dialkanoic acid is a adipic acid, azelaic acid, suberic acid, sebacic acid or 1,12-dodecandioic acid.

8. The process of claim 5 wherein the added material is added at 0° to 30° C.

9. The process of claim 6 wherein the material is added at 15°-20° C.

10. The process of claim 7 including the additional steps of removing and drying the precipitated diperoxyacid completely coated with the sulfate salt as a desensitizing agent.

11. The process of claim 4 including the additional steps of removing and drying the precipitated diperoxyacid completely coated with the sulfate salt as a desensitizing agent.

12. The process according to claim 2 wherein the added material is added until the pH rises to 3-5.5.

13. The process of claim 2 wherein the alkaline material is sodium hydroxide, magnesium hydroxide or sodium aluminate.

14. The process of claim 13 wherein the alkanedioic acid is azelaic acid and the precipitated diperoxyazelaic acid completely coated with sodium sulfate or magnesium sulfate is removed from the aqueous mixture and dried.

15. The process of claim 1 wherein the added material is added at 0° to 30° C., there is employed 2 to 20 moles of hydrogen peroxide per mole of dialkanoic acid and there is employed the added material in an amount to give a solid diperoxyacid having a peroxyacid content of 2.5 to 85.4%.

16. The process of claim 15 wherein the added material is added in aqueous solution or suspension and the process includes the steps of removing and drying the precipitated diperoxyacid coated with the sulfate salt as a desensitizing agent.

17. The process of claim 1 wherein there is employed the aromatic carboxylic acid.

18. The process of claim 17 wherein $R_1$, $R_2$, $R_3$, $R_4$ and $R_5$ are hydrogen or COOH.

19. The process of claim 18 wherein the aromatic carboxylic acid is isophthalic acid.

20. The process of claim 17 wherein the added material is an aqueous solution of sodium hydroxide, aqueous slurry of magnesium hydroxide, aqueous suspension of lithium hydroxide or aqueous solution of sodium aluminate.

21. The process of claim 17 wherein the added material is employed in an amount to give a solid diperoxyacid having a peroxyacid content of 18.0 to 85.1%.

22. The process of claim 21 wherein the starting aromatic acid is isophthalic acid.

23. The process of claim 20 wherein the added material is added at 0° to 30° C.

24. The process of claim 20 including the additional steps of removing and drying the precipitated peroxyacid completely coated with the sulfate salt as a desensitizing agent.

25. The process of claim 17 including the additional steps of removing and drying the precipitated peroxyacid completely coated with the sulfate salt as a desensitizing agent.

26. The process of claim 2 wherein the alkanedioic acid has 5 to 16 carbon atoms.

27. An aqueous composition of pH 2 to 6 suitable for forming desensitized, storage stable peroxy acid upon drying, said aqueous composition containing hydrogen peroxide and a diperoxyalkanedioic acid having 5 to 16 carbon atoms or the peroxy acid of an aromatic carboxylic acid having the formula

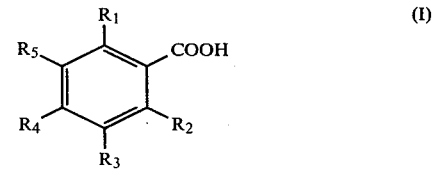

(I)

wherein $R_1$, $R_2$, $R_3$, $R_4$ and $R_5$ are hydrogen, COOH, 1-4 carbon atom alkyl, 1-4 carbon atom alkoxy or halogen and prepared by a process consisting essentially of adding to the aqueous mixture resulting from the reaction of an alkanedioic acid having 5 to 16 carbon atoms or an aromatic carboxylic acid of formula (I) with aqueous hydrogen peroxide and sulfuric acid a material which reacts with sulfuric acid to form a sulfate salt and is an alkali metal hydroxide, an alkaline earth metal hydroxide, or sodium aluminate.

28. An aqueous composition according to claim 27 wherein there is employed an alkanedioic acid having 5 to 16 carbon atoms.

29. An aqueous composition according to claim 28 wherein the added material is added in aqueous solution or suspension and in an amount such that the aqueous composition has a pH of 3 to 5.5, said process having been carried out at a temperature of 0° to 30° C.

30. An aqueous composition according to claim 27 wherein there is employed an aromatic carboxylic acid of formula (I).

31. An aqueous composition according to claim 30 wherein the added material is added in aqueous solution or suspension and in an amount such that the aqueous composition has a pH of 3 to 5.5, said process having been carried out at a temperature of 0° to 30° C.

* * * * *